United States Patent
Panetta et al.

(10) Patent No.: US 7,114,375 B2
(45) Date of Patent: Oct. 3, 2006

(54) PROCESS MONITORING AND PARTICLE CHARACTERIZATION WITH ULTRASONIC BACKSCATTERING

(75) Inventors: Paul D. Panetta, Richland, WA (US); Richard A. Pappas, Richland, WA (US); Brian J. Tucker, Pasco, WA (US)

(73) Assignee: Battelle Memorial Institute, Richland, WA (US)

(*) Notice: Subject to any disclaimer, the term of this patent is extended or adjusted under 35 U.S.C. 154(b) by 0 days.

(21) Appl. No.: 10/757,734

(22) Filed: Jan. 13, 2004

(65) Prior Publication Data

US 2005/0150275 A1 Jul. 14, 2005

(51) Int. Cl.
*G01N 29/00* (2006.01)

(52) U.S. Cl. ............ 73/61.75; 73/64.53; 73/590; 73/596; 73/597; 73/599

(58) Field of Classification Search ............ 73/61.75, 73/64.53, 590, 596, 597, 599
See application file for complete search history.

(56) References Cited

U.S. PATENT DOCUMENTS

| | | | |
|---|---|---|---|
| 3,779,070 A | 12/1973 | Cushman et al. | |
| 3,908,465 A | 9/1975 | Bartlett | |
| 4,412,451 A | 11/1983 | Uusitalo et al. | |
| 4,696,191 A | 9/1987 | Claytor et al. | |
| 4,706,509 A | 11/1987 | Riebel | |
| 4,718,269 A | 1/1988 | Der Kinderen | |
| 4,825,688 A * | 5/1989 | Kraus et al. ............ | 73/61.75 |
| 4,848,139 A * | 7/1989 | Blake-Coleman et al. . | 73/61.75 |
| 4,934,177 A * | 6/1990 | Cuthbertson et al. ....... | 73/32 A |
| 4,959,228 A * | 9/1990 | Skrgatic et al. ............ | 426/11 |
| 5,058,432 A | 10/1991 | Morkun et al. | |
| 5,121,629 A | 6/1992 | Alba | |
| 5,357,964 A | 10/1994 | Spivey et al. | |
| 5,569,844 A | 10/1996 | Sowerby | |
| 5,594,165 A | 1/1997 | Madanshetty | |
| 5,616,672 A | 4/1997 | O'Brien | |
| 5,918,272 A | 6/1999 | Snyder et al. | |
| 5,920,007 A | 7/1999 | Hirota et al. | |
| 5,922,946 A | 7/1999 | Hirota et al. | |
| 5,969,237 A | 10/1999 | Jones et al. | |
| 5,987,972 A | 11/1999 | Hirota et al. | |
| 6,029,507 A | 2/2000 | Faber et al. | |
| 6,109,098 A | 8/2000 | Dukhin et al. | |
| 6,378,357 B1 | 4/2002 | Han et al. | |

(Continued)

OTHER PUBLICATIONS

Ishimori, Y. et al., "Determination of Microbial Populations with Piezoelectric Membranes", Applied and Environmental Microbiology, vol. 42, No. 4, Oct. 1981, pp. 632-637.*

*Primary Examiner*—Daniel S. Larkin
(74) *Attorney, Agent, or Firm*—Klarquist Sparkman, LLP

(57) ABSTRACT

A fermention process is monitored by detecting ultrasound backscattered from the cells as a function of time. A transducer 46 is placed in a fermentor 30 and transmits ultrasound towards a reflecting surface 50. The transducer receives that portion of the ultrasound which reflects from the reflecting surface 50, as well as that portion of the ultrasound which backscatters from cells 34 between the transducer 46 and the reflecting surface 50. Signals from the transducer are conditioned and subsequently processed to provide output to a controller regarding the status of the fermentation process in real time. The backscattering measurements can be used to determine a growth phase transition, such as the transition between the logarithmic growth phase of the cells and their stationary phase.

26 Claims, 8 Drawing Sheets

U.S. PATENT DOCUMENTS

| | | |
|---|---|---|
| 6,397,734 B1 * | 6/2002 | Atzinger ............... 99/468 |
| 6,401,538 B1 | 6/2002 | Han et al. |
| 6,423,007 B1 | 7/2002 | Lizzi et al. |
| 6,449,563 B1 | 9/2002 | Dukhin et al. |
| 6,481,268 B1 | 11/2002 | Povey et al. |
| 6,487,894 B1 | 12/2002 | Dukhin et al. |
| 6,508,104 B1 | 1/2003 | Deluca et al. |
| 6,598,466 B1 | 7/2003 | Deluca et al. |
| 6,604,408 B1 | 8/2003 | Dosramos et al. |
| 6,698,276 B1 | 3/2004 | Povey et al. |
| 6,796,195 B1 * | 9/2004 | Povey et al. ............. 73/865.5 |
| 6,874,356 B1 * | 4/2005 | Kornfeldt et al. .......... 73/64.42 |
| 2003/0051535 A1 | 3/2003 | Coupland et al. |
| 2004/0060356 A1 | 4/2004 | Scott |
| 2004/0090625 A1 * | 5/2004 | Fischer et al. ............ 356/336 |

* cited by examiner

PROCESS MONITORING AND PARTICLE CHARACTERIZATION WITH ULTRASONIC BACKSCATTERING

TECHNICAL FIELD

The present invention is generally related to particle characterization using ultrasonic backscattering and/or diffuse field measurements. A particular, but not exclusive, application involves the rapid and non-invasive characterization of industrial scale fermentation processes.

BACKGROUND

Suspensions or slurries having moderate and high particle concentrations are found in a variety of industries such as chemical and pharmaceutical manufacturing and waste remediation. As the characteristics of the suspensions have considerable influence on production costs, product quality and yield, there is a continual need to rapidly, cost-effectively, and non-invasively characterize these suspensions in real time. The present invention is generally directed to addressing this need.

In particular, a variety of industrial processes rely on the biological functioning of cells. For example, industrial scale fermentation processes are encountered in various pharmaceutical and chemical industries, and typically involve fungi, bacteria, or mammalian cells that biologically convert raw materials (nutrient broth) into a desired product. Examples are ethanol fermentation using yeast, human insulin production using bacteria or yeast, and human Factor VIII using mammalian cells. While the individual cells are typically tailored to produce a specific product under controlled conditions, there is a need to know the fermentation conditions, such as the number of cells per volume, their size and size distribution, and the fraction of cells that are alive (i.e. cell viability) in order to ensure accurate control and reproducibility. Past efforts at monitoring the cells during industrial fermentation has required physical extraction of samples from the fermentor and off-line processing, such as optical density (absorption) measurements. Not only is the withdrawal of a sample from a fermentor time consuming and potentially disruptive, but optical density measurements are generally only effective over a narrow region of cell concentration. Therefore, additional sample preparation, such as dilution, is often required to achieve proper characterization, increasing the potential for error, cost, and complexity of process monitoring. Accordingly, improvements are needed, and in one or more embodiments, the present invention addresses these and other concerns.

SUMMARY

The present invention provides systems and techniques for characterizing suspensions, in particular the cells and surrounding medium in an industrial fermentor. While the actual nature of the invention covered herein can only be determined with reference to the claims appended hereto, certain aspects of the invention that are characteristic of the embodiments disclosed herein are described briefly as follows.

According to one aspect, the present invention provides for the monitoring of a fermentation process by detecting ultrasound backscattered from the cells. It has been found that detection of backscattering as a function of time provides a mechanism to detect a growth phase transition of the cells, such as between the logarithmic growth phase and the stationary phase, in real time.

In another aspect, an ultrasonic transducer is positioned insider a fermentor to transmit ultrasound towards a reflecting surface for the monitoring of a population of cells. During monitoring, the transducer receives that portion of the ultrasound which reflects from the reflecting surface, as well as that portion of the ultrasound which backscatters from cells that are positioned substantially between the transducer and the reflecting surface. Signals from the transducer are conditioned and subsequently processed to provide output to a controller regarding the status of the fermentation process.

These and other aspects are described more fully below.

BRIEF DESCRIPTION OF THE FIGURES

Although the characteristic features of this invention will be particularly pointed out in the claims, the invention itself, and the manner in which it may be made and used, may be better understood by referring to the following description taken in connection with the accompanying figures.

DESCRIPTION OF THE ILLUSTRATED EMBODIMENTS

Figure 1:
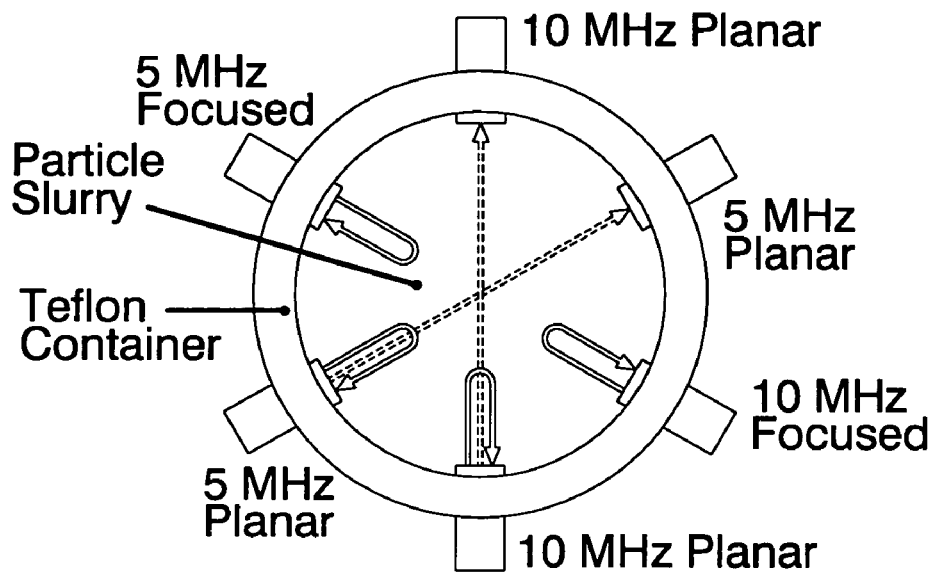
FIG. 1 is a top diagramatic view of a container and transducer array for performing ultrasonic backscattering, attenuation and velocity measurements on the suspensions.

For the purposes of promoting an understanding of the principles of the invention, reference will now be made to the embodiments illustrated in the drawings and specific language will be used to describe the same. It will nevertheless be understood that no limitation of the scope of the invention is hereby intended. Alterations and further modifications in the illustrated devices, and such further applications of the principles of the invention as illustrated herein are contemplated as would normally occur to one skilled in the art to which the invention relates.

In a general form, the present invention is an approach to characterizing slurries based on ultrasound backscattering, diffuse field measuremenets and attenuation measurements. While a particular application involves the characterization of a fermentation process, it is to be understood that the invention can be applied to characterize a variety of particle mixtures, such as those utilized in food, petrochemical/polymer, pharmaceutical, waste remediation, and other industrial processes. Accordingly, the general approach to slurry characterization will first be described followed by the more particular application to fermentation monitoring.

Many existing techniques for the ultrasonic characterization of slurries and suspensions are based on ultrasonic attenuation and its dependence on ultrasonic frequency. For example, Allegra and Hawley "Attenuation of Sound in Suspensions and Emulsions: Theory and Experiments." *The Journal of the Acoustical Society of America*, 51(5): 1545–1564 (1972) provides a theoretical treatment for solid-liquid suspensions. Their model accounts for the attenuation due to viscous damping, as the particle moves and changes shape, the thermal loss as heat is exchanged between the ultrasonic field and the particle, and the scattering loss as the propagating wave is scattered at the interfaces between the fluid and the solid particles. However, they obtained good agreement between experimental measurements of attenuation and theoretical predictions only at low concentrations. A potential reason for this is that their theory does not incorporate particle size distributions or contributions from multiple scattering. While recent work by Spelt and Naraoto have included some degree of multiple scattering, the validity and numerical stability are limited to low concentration. (Spelt, P. D. M., et al., "Determination of Particle Size Distribution from Acoustic Wave Propagation Measurements." Physics of Fluids, 1(5) 1065 (1999))

The mathematical inversion of a frequency-dependent ultrasonic attenuation theory is often a limiting factor in slurry characterization, particularly in situations where the nature of the particle size distribution and physical properties of the particles are not known a priori. Furthermore, there are mechanical complications that can arise when careful transducer alignment is required, for example to orient a pair of transducers in a 180° or diametrically opposed orientation.

To overcome these difficulties, the approach of the present invention employs the use of ultrasonic backscattering and/or measurements of the diffuse field properties. It is believed that these measurements can expand the dimensionality of the measured data and extend the associated modeling to form the basis of the new approach to slurry characterization.

An ultrasonic backscattering measurement is attractive because viscous, thermal, and inertial effects have small contributions to backscattering. Furthermore, backscattering theories are less complicated than attenuation theories and lend themselves to more stable inversion processes. Moreover, since the measurements of backscattering and diffuse fields do not require long travel distances of the ultrasound through the slurry, they can be performed in moderately or highly concentrated slurries and with a single transducer so as to avoid the alignment and stability problems of pairs of transducer.

To demonstrate the present approach, particle slurries with concentrations up to 40 weight percent (0, 5, 10, 15, 20, 30, and 40) were created by mixing glass particles (35 and 70 μm mean diameter) in deionized, degassed water. A cylindrical, 10.2-cm (4-in.) inside diameter, Teflon container containing opposing transducers as shown schematically in FIG. 1 was then used to obtain velocity, attenuation, and backscatter measurements. Backscatter measurements were obtained with four different transducers in pulse-echo mode: 5-MHz planar, 5-MHz focused at 0.79 cm (2.0 in.), 10-MHz planar, and 10 MHz focused at 0.60 cm (1.5 in.). Velocity and attenuation measurements were obtained in a pitch-catch configuration with a pair of both 5-MHz and 10-MHz planar transducers. Deionized, degassed water was used to align the through-transmission transducers and also as a reference liquid for subsequent attenuation measurements, and a high-speed mixer (not shown) agitated the slurry to keep the particles in suspension during measurements.

A RITEC SP-801 pulser was used to excite the transducers and a RITEC BR-640 receiver was used to amplify and filter the received signals. The pulser was set to optimally excite the transducers with a square wave pulse dependent on the nominal transducer frequency response. The receiver gain was set to 64 dB for backscatter measurements and varied between −8 dB and 52 dB for through-transmission attenuation measurements. An input impedance of 50 Ohms was used with a bandpass filter between 1 and 12 MHz. For pulse-echo applications, a RITEC RDX-2 was used with a damping of 1300 Ohms and a low frequency cutoff of 1.6 MHz. Signals were captured at a sampling rate of 100 MHz, with a LeCroy 9310M oscilloscope and stored digitally on a computer via a GPIB communications port utilizing a Labview data acquisition program.

For the pitch-catch velocity and attenuation measurements, 50 RF waveforms were averaged for each weight percentage. This signal was used to measure transit time (time to highest positive peak) and attenuation relative to water. The Fourier amplitude of each averaged signal was calculated, $\Gamma_s(f)$ and compared with a baseline Fourier amplitude from water, $\Gamma_{ref}(f)$, to calculate the attenuation as a function of frequency, $\alpha(f)$, using the following expression where z is the through-transmission distance and $D_s$ and $D_{ref}$ are the beam diffraction corrections for sample and water reference, respectively:

$$a(f) = \frac{1}{z}\ln\left[\frac{D_s(f)\Gamma_{ref}(f)}{D_{ref}(f)\Gamma_s(f)}\right] \quad (1)$$

For these samples, the diffraction corrections were assumed to be the same for both the slurries and the water reference. This assumption is reasonable considering that the velocity of the highest concentration slurry varies from water by only a few percent For backscattering measurements, 100 single-shot signals were captured at each concentration. The Fourier amplitude was calculated from a small time window of each RF waveform. The Fourier amplitude at each frequency was then averaged for all 100 waveforms. Since attenuation caused a diminution of the backscattered signals, this measure of the backscattering was corrected by fitting each attenuation spectra with a power law function within the frequency bandwidth of the transducer. The backscattered signal was then corrected for the attenuation by multiplication by a function dependant on the frequency dependant attenuation times the distance the sound wave traveled.

Figure 2:
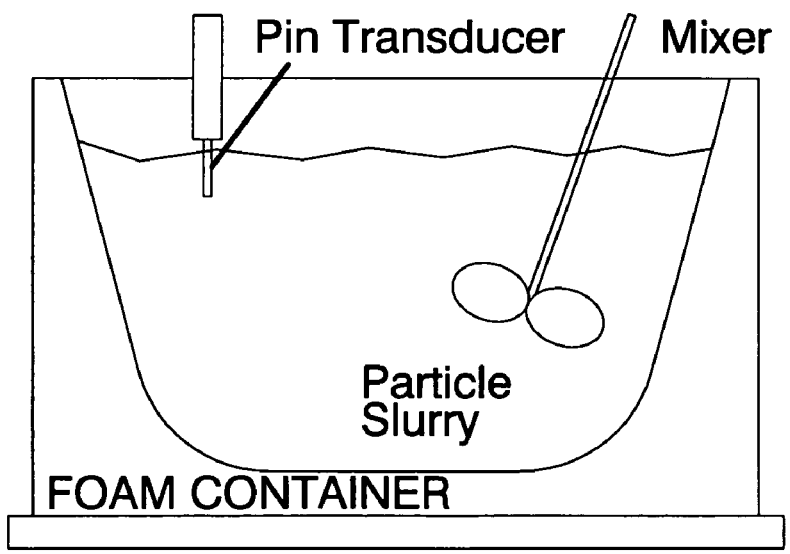
FIG. 2 is side diagramatic view of the container for performing the diffuse field measurements on the suspensions.

A foam container was constructed to conduct diffuse field measurements as depicted in FIG. 2. Particle weight percentages were the same as those used in the backscatter measurements. A RITEC SP-801 pulser and BR-640 receiver were used to drive a Valpey-Fisher transducer, with a nominal diameter of 1 mm, in pulse-echo mode to measure the diffuse field signals. The pulser sent a 1-MHz, 400-volt square wave pulse to the transducer with a 25 Hz repetition rate. The diplexer was set at a damping of 1300 Ohms and a low frequency cutoff of 30 kHz. The receiver gain was set to 56 dB with a high input impedance and a bandpass filter between 500 kHz and 3 MHz. Five RF waveforms were averaged and captured at a sampling rate of 50 MHz. A joint time frequency analysis was performed on the received RF waveforms as detailed in Weaver, R. and Sachse W. "Diffusion of Ultrasound in a Glass Bead Slurry." *Journal of the Acoustical Society of America*, 97: 2094–2102 (1995). The decay rate of the diffuse field was determined as a function of frequency from the resultant amplitudes for each frequency window.

Figure 3:
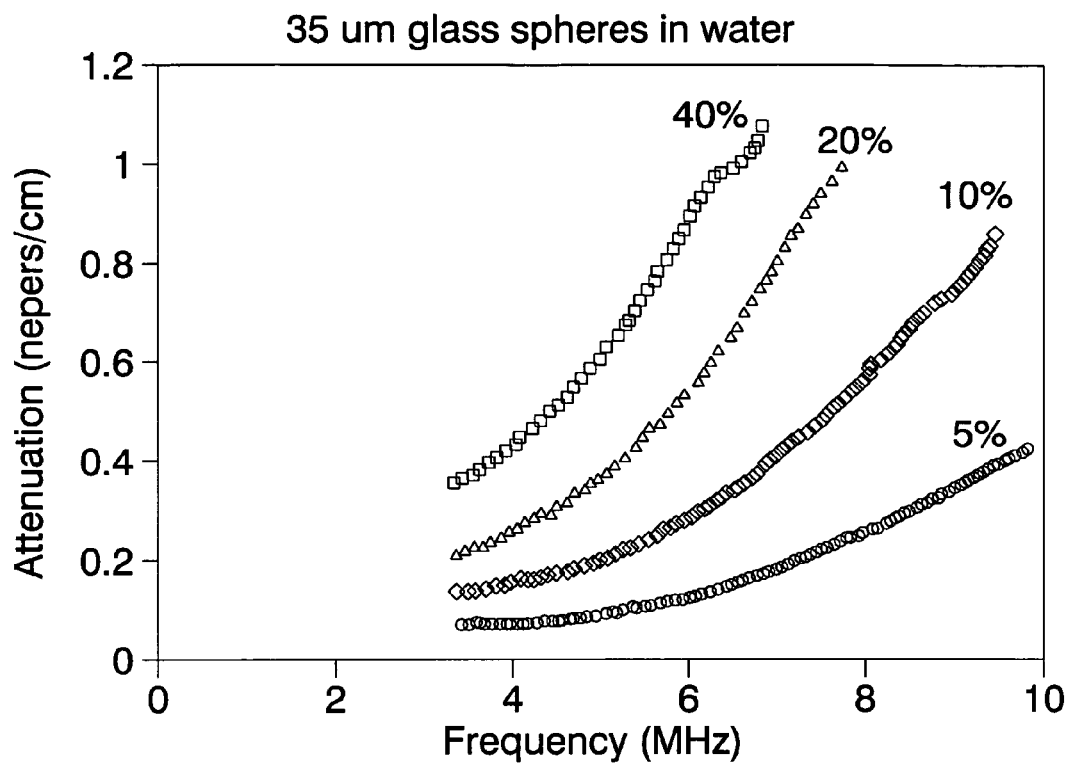
FIG. 3 is a representative plot of attenuation versus frequency for 35 μm glass spheres in water at 5, 10, 20 and 40 wt %.
Figure 4:
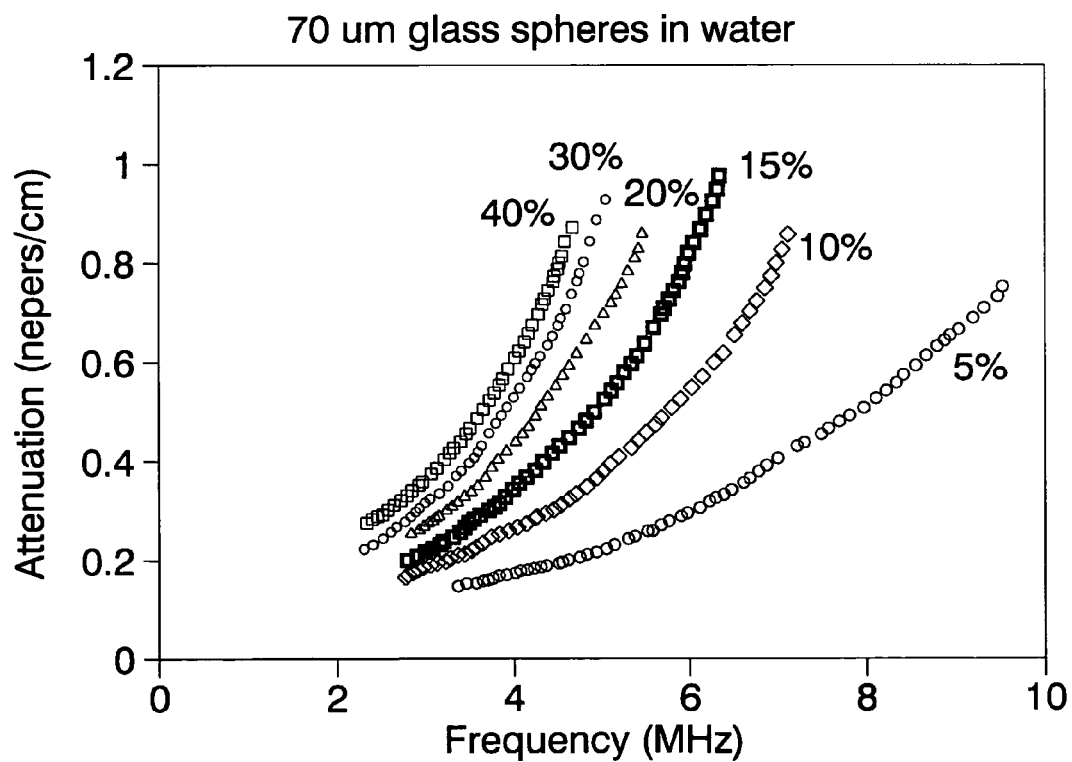
FIG. 4 is a representative plot of attenuation versus frequency for 70 μm glass spheres in water at 5, 10, 15, 20, 30 and 40 wt %.
Figure 5:
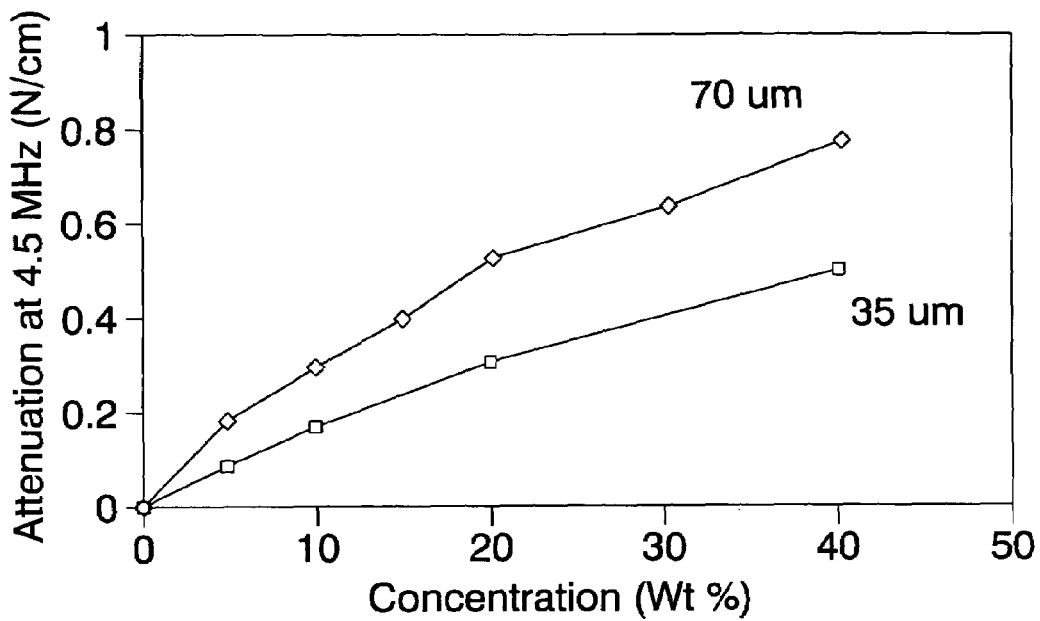
FIG. 5 is a representative plot of attenuation versus weight percent solids for 35 and 70 μm glass spheres in water.

The measured attenuation as a function of frequency for 35 μm and 70 μm glass spheres at concentrations up to 40 wt % are shown in FIGS. 3 and 4 respectively, and the measured attenuation at 4.5 MHz as a function of concentration is plotted in FIG. 5 for both the 35 and 70 μm spheres. As expected, the higher the concentration and particle size, the higher the attenuation, though a linear relationship is lacking, particularly at higher concentrations.

Figure 6:
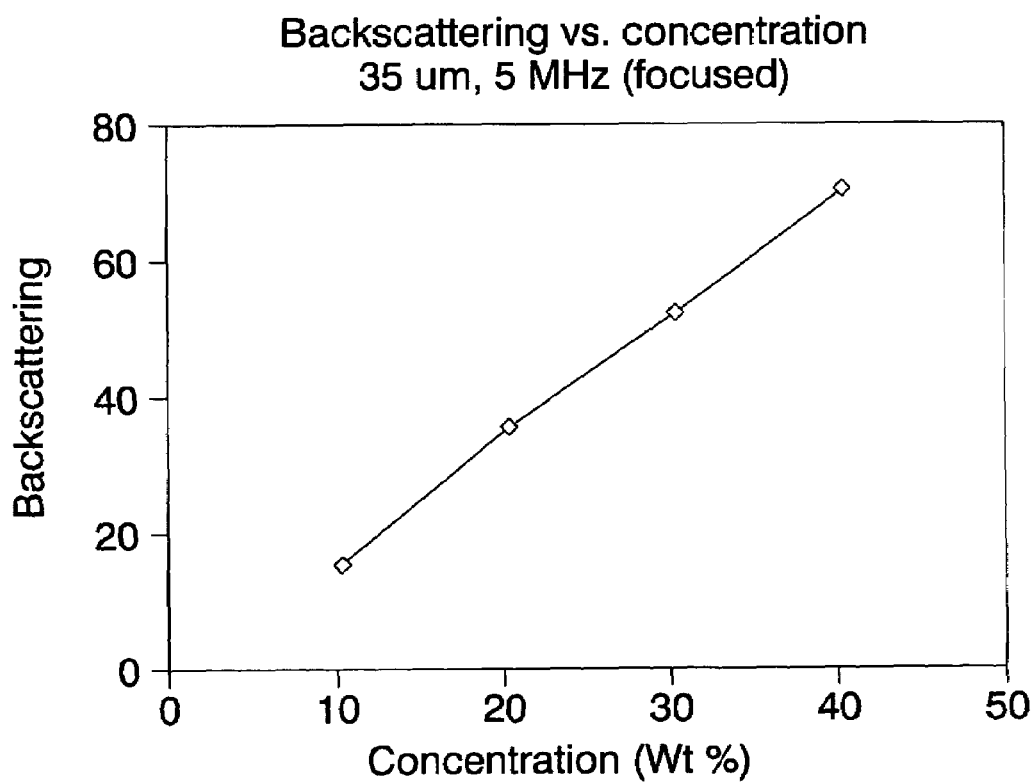
FIG. 6 is a representative plot of backscattering versus weight percent solids for 35 μm glass spheres in water.
Figure 7:
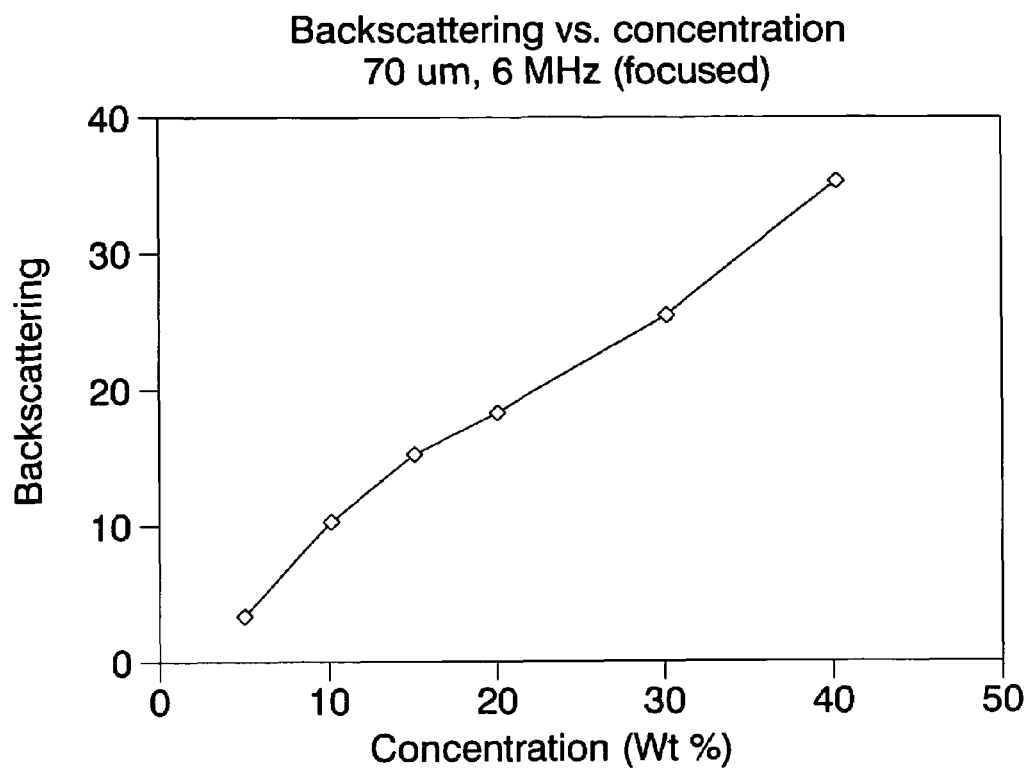
FIG. 7 is a representative plot of backscattering versus weight percent solids for 70 μm glass spheres in water

The attenuation corrected backscattering at 5 MHz is plotted in FIG. 6 for the 35 μm spheres and is plotted in FIG. 7 for the 70 μm spheres at 6 MHz. The backscattering is seen to substantially linearly increase as a function of concentration for both the 35 μm and the 70 μm glass spheres.

Figure 8:
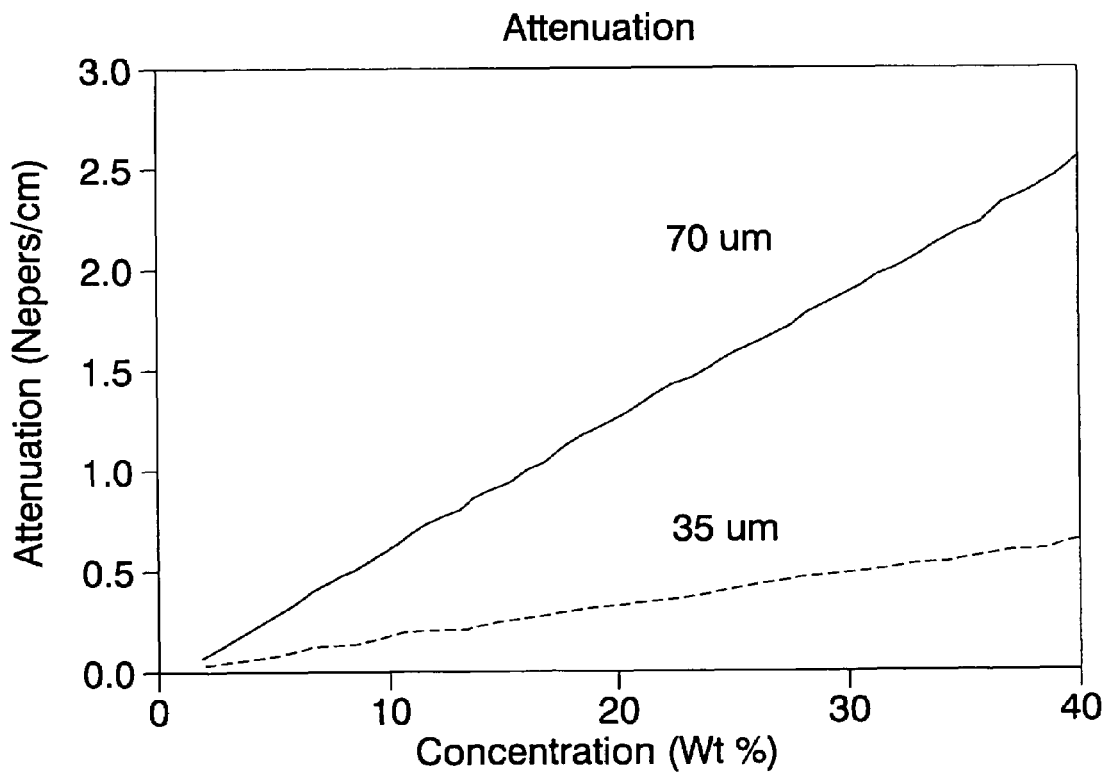
FIG. 8 is a plot of the theoretically predicted attenuation versus weight percent for 35 and 70 μm glass spheres in water.
Figure 9:
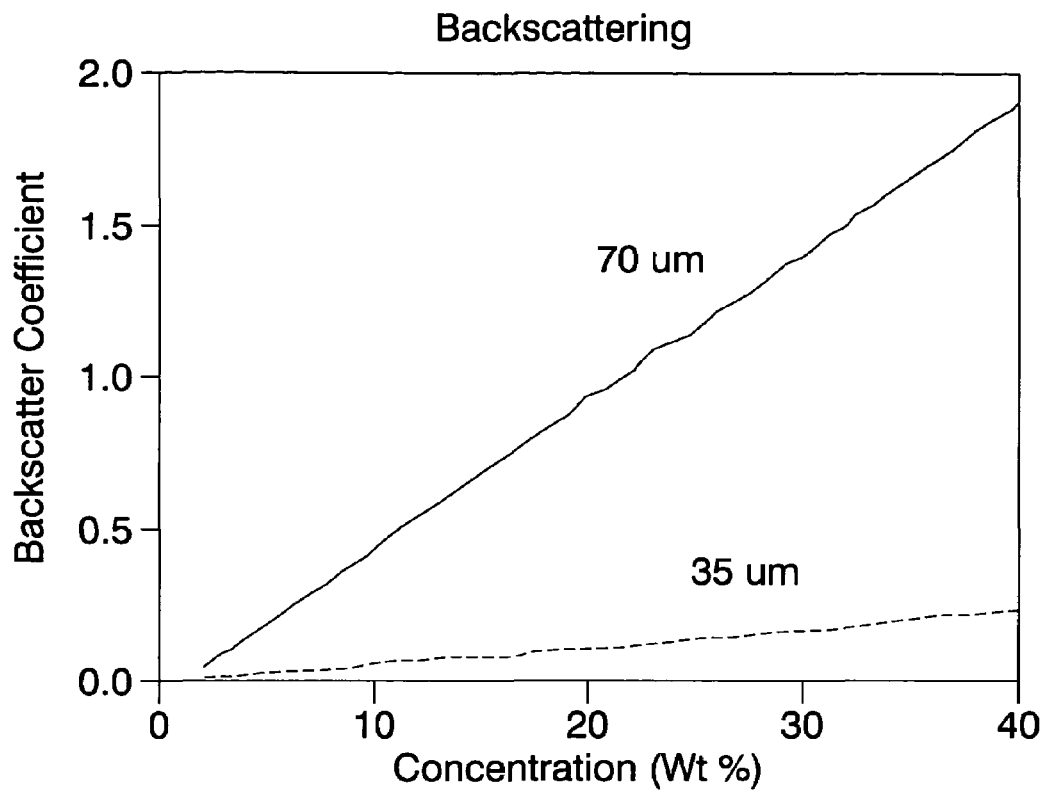
FIG. 9 is a plot of the theoretically predicted backscattering versus weight percent for 35 and 70 μm glass spheres in water.

Theoretical predictions for the attenuation and backscattering are plotted in FIGS. 8 and 9, showing consistency with the measured results but greater qualitative agreement with the backscattering results.

Figure 10:
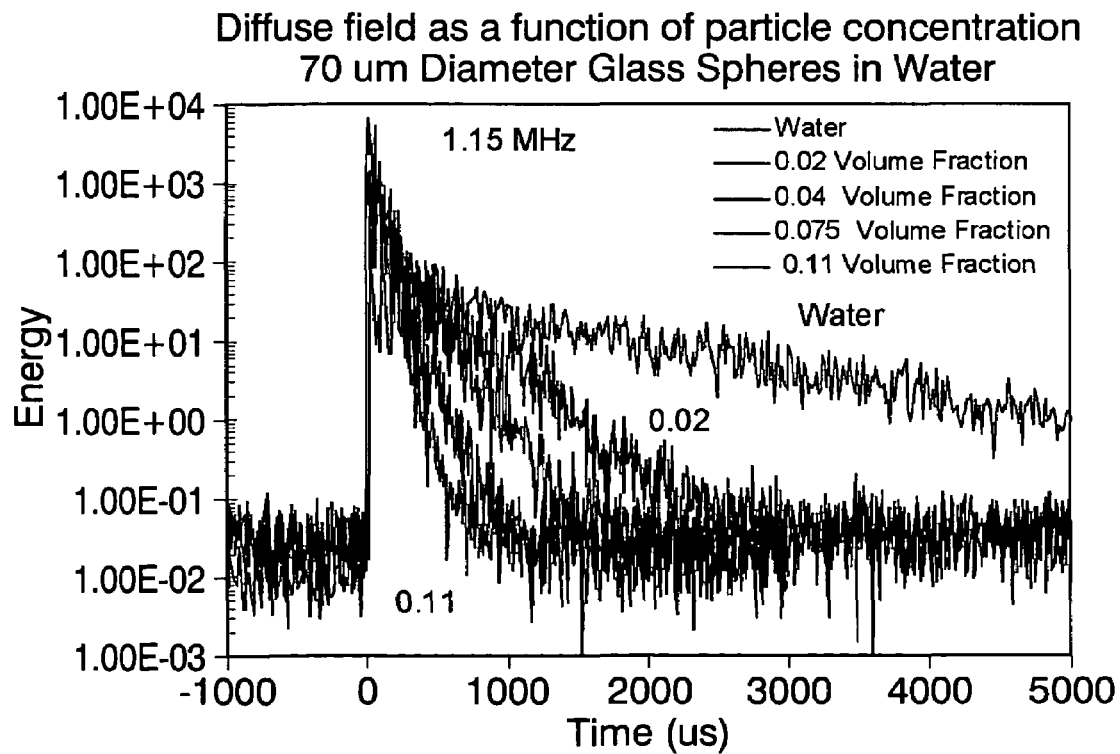
FIG. 10 is a representative plot of the response received at the transducer in the FIG. 2 system as a function of time after pulse excitation for various volume fractions of glass particles in water.
Figure 11:
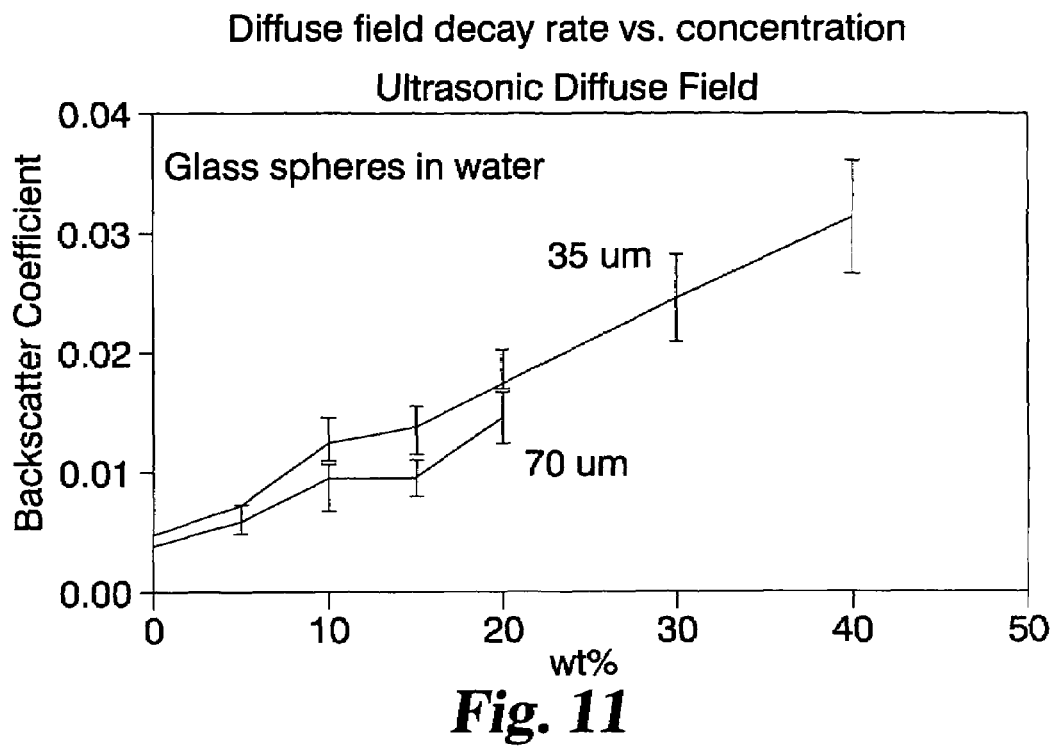
FIG. 11 is a representative plot of calculated diffuse field decay rate as a function of weight percent solids for 70 and 35 μm glass spheres in water.

The diffuse field results are shown in FIG. 10, with the particle weight fractions converted to volume fractions. As can be seen, the measured "energy" decays as a function of time after the initial excitation pulse. The diffuse field data were modeled to extract a characteristic decay rate, and this decay rate is plotted as a function of concentration in FIG. 11. It can be seen that the decay rate increases as the concentration increased. The diffuse filed could also have been measured by transducers in a pitch catch mode, wherein the diffuse field response would have been expected to show a brief period of energy buildup before this characteristic energy decay.

Having demonstrated the effectiveness of backscattering and diffuse field measurements to correlate to particle concentration, empirical and theoretical models can now be employed to correlate these measurements with the characteristics of suspensions and slurries having unknown properties. For example, calibration charts can be developed for the backscattering and the ultrasonic diffuse field measurements.

Attenuation measurements can also be made in the conventional fashion to provide redundant data where the attenuation theories are accurate (at low concentration). Alternatively, measurements of the frequency dependence of attenuation can be employed to provide an indication of the scattering regime of the suspension. Attenuation generally depends on the frequency, f, the particle size, α, and the viscosity of the fluid μ, and the frequency dependence is classified in three specific regimes: the viscous regime (ka<<1), the inertial damping (ka around 1) and the scattering regime (ka >>1). In the viscous regime, the attenuation is proportional to $f^2\alpha^2/\mu$; in the inertial $(\mu f)^{1/2}/a$; and in the multiple scattering regime $f^4$.

According to an aspect of the invention, backscattering and/or diffuse field theories are constructed for each of the different scattering regimes. For an unknown slurry, attenuation measurements (i.e. attenuation as a function of frequency) are used to select the appropriate theory, and having selected the appropriate theory, backscattering and/or diffuse field measurements are fit to the selected model to characterize the slurry. It is believed that independent identification of the scattering regimes via attenuation measurements permits the selection of the correct backscattering theory approximation and the stable mathematical inversion thereof to determine the particle size and concentration absolutely. Accordingly, in this form it will be appreciated that, the present invention is a technique for slurry characterization wherein a model of backscattering and/or diffuse field measurements on an unknown slurry is selected from several candidate models based on the measured attenuation of the slurry. Then from the selected backscattering and/or diffuse field based model and actual measurements of the backscattering and/or diffuse field of the slurry, unknown characteristics of the slurry are obtained.

The theories employed can be empirical or theoretical models for the interaction of ultrasound with the slurries. In constructing these models, backscattering measurements can provide three parameters related to particle size and concentration. One is the amplitude of the backscatter at a fixed frequency, and the second is the frequency dependence of the backscattering. A third parameter is the change of the backscattering amplitude as a function of time after the excitation pulse, i.e. a measure of the backscattering from particles at varying distances from the transducer face (backscattering from the close particles occurring at short times with scattering from more distant particles occurring at longer times). For attenuating suspensions, the measured amplitude of the backscattering response decays as a function of time as the pulse has traversed more of the suspension. However, it has been found that correcting the time dependent backscattering response for expected losses from attenuation, for example by multiplying the RMS average of the amplitude by exp(attenuation*distance) wherein distance is given by velocity*time, reveals a function that, at least for higher particle concentrations, is increasing over time. Moreover, the rate of increase in this attenuation corrected backscattering as a function of time has been found to increase with increasing particle concentration, providing yet another parameter for correlation with or incorporation into the models of suspension properties.

The diffuse field can provide two parameters for use in characterizing a solid-liquid suspension. If measured in the pitch-catch mode, a first parameter can be the initial buildup of the square of the (Fourier) amplitude as a function of time in the early time regime after an excitation pulse. The second parameter is the decay in the square of the Fourier amplitude as a function of time at longer times after the excitation pulse. When measured in pulse echo mode, the diffuse field data will yield only this second parameter.

Having outlined the general approach to applying backscattering and diffuse field measurements for characterizing particle slurries and suspensions, a more specific application is now described. According to an aspect of the present invention, ultrasonic backscattering measurements are used to non-invasively measure the physical properties of cell populations, for example *Escherichia coli*, (*E. coli*), yeast (*Saccharomyces cerevisiae*) or filamentous fungal cell populations, during fermentation. This ultrasonic monitoring method can out-perform an existing optical technique (optical density (OD) measurements) in opaque media at certain conditions, as will be described below. Moreover, results can be obtained instantaneously (in less than 1 minute) online, while optical measurements requiring direct sampling and dilution might require up to 10 minutes per sample. The ability to obtain cell growth measurements without sampling the fermentor saves valuable culture material, eliminates the chance of contaminating the fermentation with undesirable microbes, and limits the uncertainty due to multiple dilutions. In addition, since the ultrasonic measurement does not require user intervention, it can easily be automated, unlike the procedure for measuring optical density (OD). Accordingly, the present invention can provide the sensitive, real-time, non-disruptive process monitoring required in the optimization of biological processes on an industrial scale.

Figure 13:
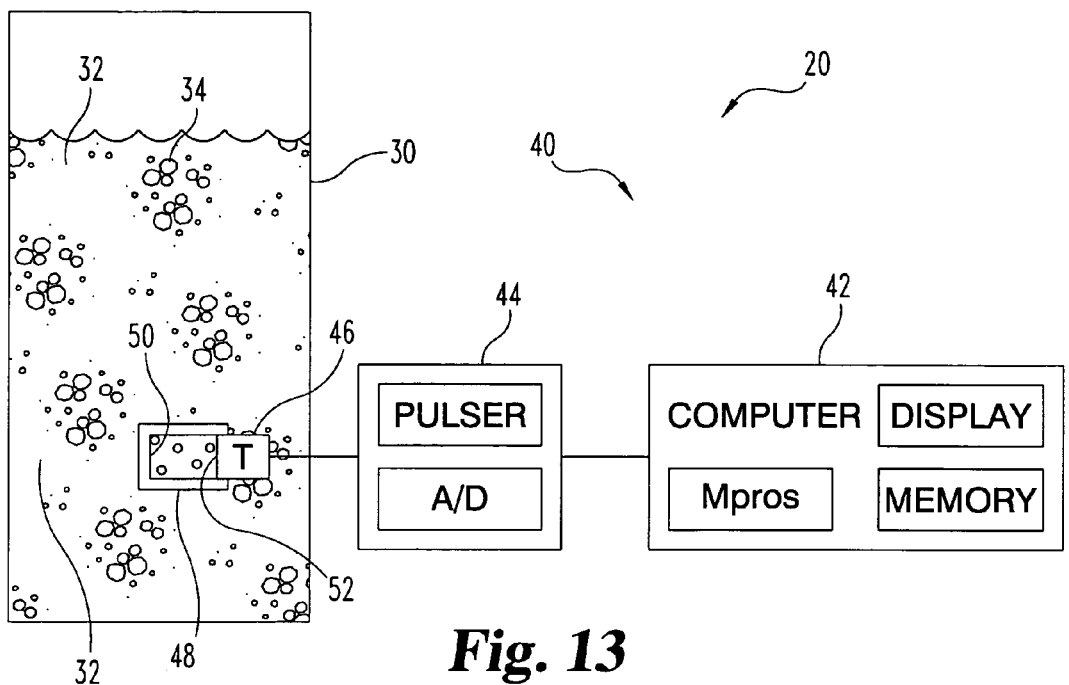
FIG. 13 is a general schematic diagram of a fermentation monitoring system of the present invention.

Turning now to FIG. 13, a schematic illustration of a fermentation monitoring system 20 is depicted. A fermentor 30 contains a population of cells 34 in a surrounding nutrient medium 32 or broth. A single transducer 46 is inside the fermentor 30 and an open reflector 48 is connected to the transducer 46 to enable ultrasonic measurements to be obtained while allowing the cells 34 and medium 32 to flow freely between the transducer face 52 and an opposed reflecting surface 50. A computer system 40 is coupled to the transducer 46 including signal collection electronics 44 and a processing system 42 to operate the transducer and collect measurements during fermentation.

System 20 is operated by measuring the attenuation, velocity and the degree of backscattering from the fermentation culture, i.e. the cells 34 and medium 32, during fermentation. While there can be considerable variation in the starting ingredients and operating parameters depending on the type of fermentation being performed, in general, to begin a batch fermentation process, the fermentor 30 is inoculated with number of the chosen cells 34 and the appropriate medium 32 or nutrient broth in the conventional fashion. The cells 34 then typically undergo an initial rapid growth phase, termed the logarithmic growth phase, wherein the number and the size of the cells 34 increase. After a time, a stationary phase is reached, wherein the cell count plateaus and the size of the cells 34 decreases to a more "normal" size. As described more fully below, it has been found that measurement of ultrasonic backscattering provides a mechanism to continuously monitor cells during the growth phase and to determine important transitions such as the cessation of the growth phase. This mechanism is based on the observation that ultrasonic backscattering increases as the cell size and number per volume increase during logarithmic growth, and that the backscattering plateaus as the number of cells per volume plateaus and the cell size returns to "normal" as the stationary phase is reached. As such, one useful empirical model according to the present invention involves the correlation of the amplitude of measured backscattering with cell size and/or number such that, under constant measurement conditions, an increase in measured backscattering indicates an substantial increase in cell size and/or number, a decrease in measured backscattering means a substantial decrease in cell size and/or number. In this model, a generally constant value for the measured backscattering can indicate steady state conditions, or where size is decreasing but number is decreasing.

Figure 14:
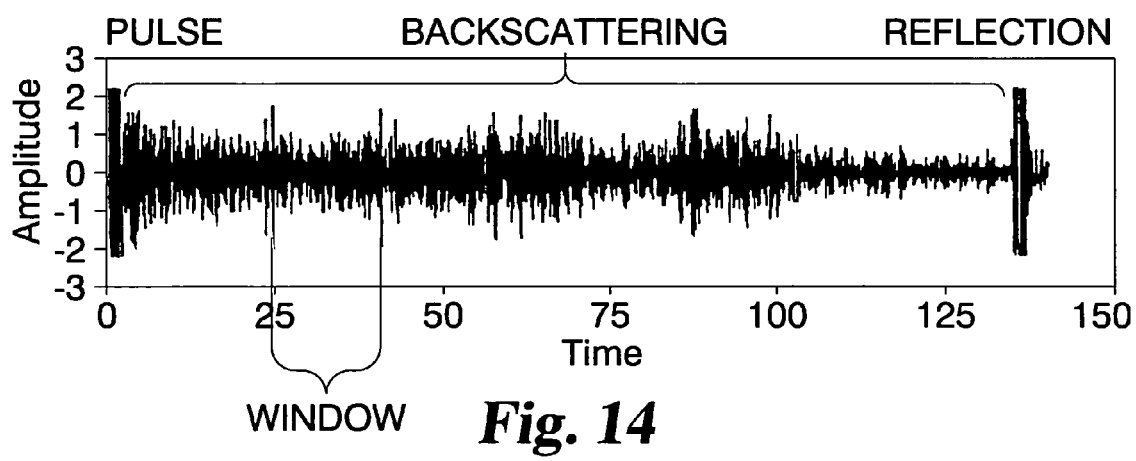
FIG. 14 is a representative plot of the measured signal amplitude as a function of time for the FIG. 13 system.

Ultrasonic measurements were performed in accordance with the FIG. 13 system utilizing a 2.5 liter New Brunswick BioFlo 3000 fermentor. The fermentation of *E. coli* DH-5a in a Terrific Broth (TB) medium at 37° C. with 250 rpm agitation was monitored for 21 hours. The ultrasonic transducer 46 employed was commercially obtained having a face 0.5 inches in diameter and a focal length of 1.0 inches. The reflector was constructed of stainless steel and positioned to provide a distance of 1.5 inches between the transducer face 52 and the reflecting surface 50. An exemplary amplitude trace of the response at the transducer 46 as a function of time after a pulse excitation is depicted in FIG. 14 and shows the initial pulse, the backscattering response, and the reflection from the reflecting surface 50. The backscattering was measured as the RMS average of the Fourier amplitude of RF waveforms in a small time gate (i.e. window). The window was selected to be centered at 2 times the transducer focal length divided by the speed of sound so as to detect the backscattering from particles located in the focal zone of the transducer.

For comparison purposes, periodic samples were taken from the fermentor and their optical density was determined at 600 nm with a Hitachi U2000. In certain cases, direct measures of cell counts were made from the extracted samples after growth on a nutrient agar and direct counts of stained specimens.

Figure 12:
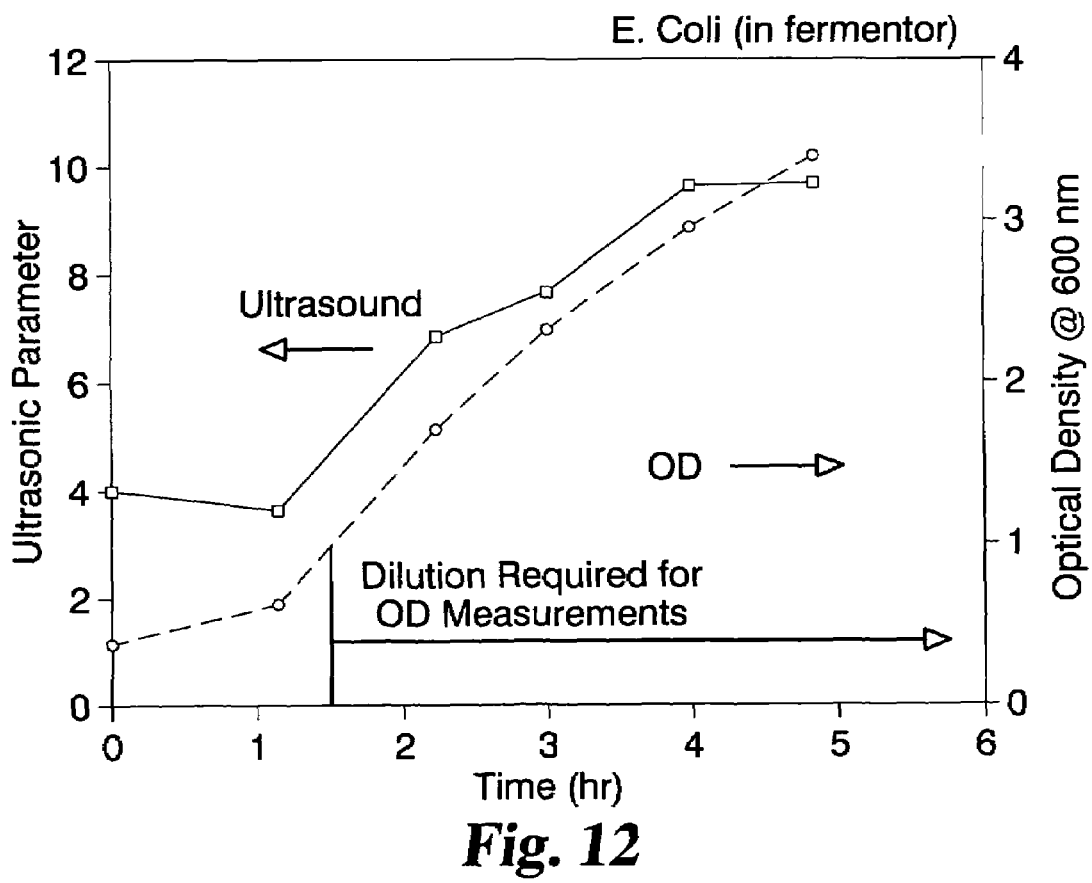
FIG. 12 is a representative plot of measured ultrasonic backscattering (left axis-solid line) and optical density (right axis-dashed line) of E. coli samples as a function of fermentation time.

During the logarithmic growth phase, the measured backscattering was seen to increase as the time increased, and correlated well with traditional optical density measurements as shown in FIG. 12. Importantly, while the OD measurements were performed on samples extracted from the fermentor and required dilution after reaching an OD of about 1 (about 1.5 hours), the ultrasonic backscattering measurements were performed in situ and without dilution for the entire fermentation process. In addition, it was found that the backscattering signal reached a plateau (not shown) upon reaching the stationary grown phase, providing a means to identify the transition between growth phases that is an important part of process monitoring.

The particular ultrasonic parameters employed will be application specific. However, it is believed that for typical applications, measurement of backscattering at a frequency range of between 1 and 100 MHz, for example between 5 and 35 MHz can be employed. Flat or unfocused transducers can be employed. In certain forms, focused transducers are employed, for example having focal lengths between about ⅛ and 3 inches. When using a focused transducer the time window for selecting the backscattering can be selected so as to capture the backscattering from cells spaced from the transducer a distance between about 50% and 150% of the focal length, more preferably about 75 and 125% of the focal length. For planar transducers the entire duration of the backscattering can be employed.

Figure 15:
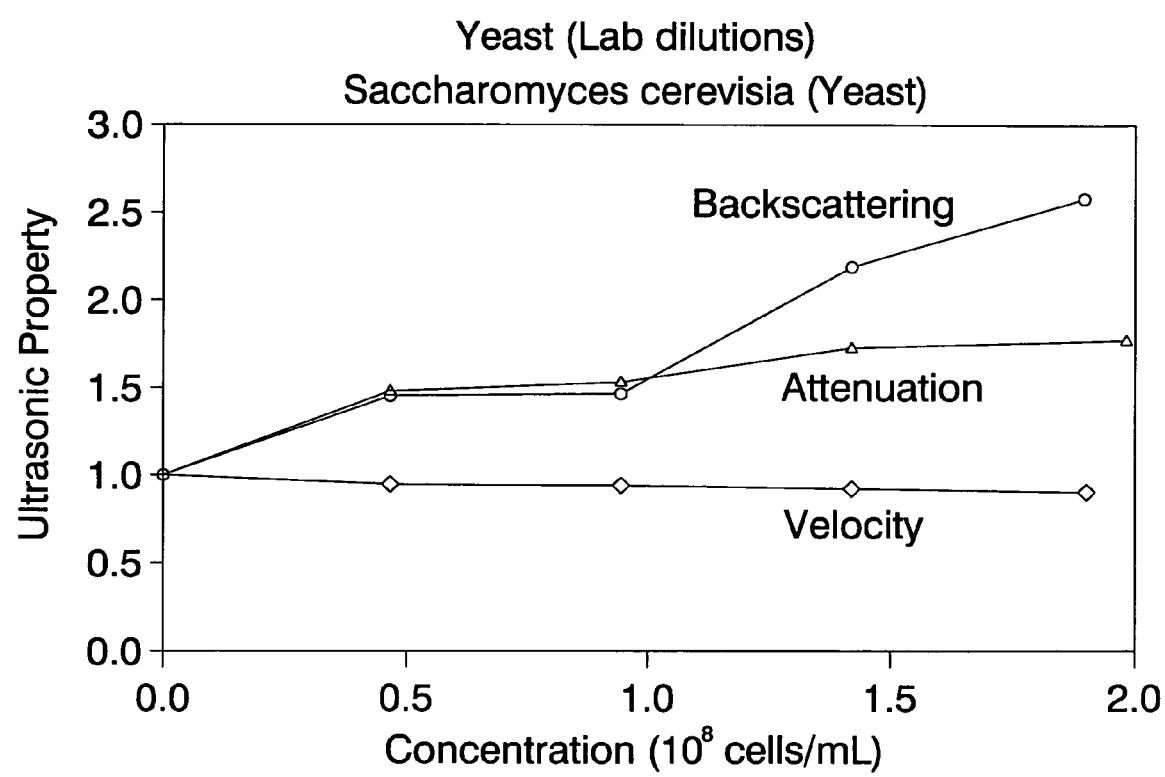
FIG. 15 is a representative plot of relative backscattering, attenuation and velocity as a function of yeast cell concentration for an exemplary yeast cell fermentation broth.

Ultrasonic measurements were also performed on yeast cells taken from a fermentation process under various laboratory dilutions. FIG. 15 contains representative plots of backscattering, attenuation and velocity are provided as a function of yeast cell concentration, where all ultrasonic values are expressed relative to the value for the broth alone (zero concentration). As between the various ultrasonic measurements, the backscattering measurements showed the greatest sensitivity to cell concentration, demonstrating their usefulness as a process indicator for fermentation monitoring.

While the transducer 46 of system 20 (FIG. 13) is positioned entirely inside the fermentor 30, the transducer 46 may also be mounted on a wall of the fermentor 30, for example having face 52 flush with an interior wall of the fermentor 30. In other variations, transducer 46 is mounted with face 52 flush with an exterior wall of the fermentor 30 or partially penetrating the wall and ultrasonically communicates with the contents of the fermentor 30 through an exterior wall of the fermentor. In these and other variations, an opposing wall of the fermentor 30 can serve and the reflecting surface 30 for purpose of taking the attenuation and velocity measurements. Alternatively or in addition, velocity and attenuation measurements are taken with a separate transducer setup or not at all during the fermentation process.

Alternatively or in addition to tracking cell growth during batch fermentation as described above, the present technique can be employed during continuous process of fermentation and other industrial processes where a set point, target value or stationary phase needs to be maintained. In this form, the backscattering measurement is fed to a process controller programmed to make appropriate adjustments to maintain the measured backscattering within a predetermined range.

CLOSURE

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

What is claimed is:

1. A method comprising monitoring a fermentation process of a population of cells in a suspension or slurry by detecting ultrasound backscattered from the cells in the suspension or slurry, wherein the cells are selected from the group consisting of bacteria, yeast cells, fungi, and mammalian cells.

2. The method of claim 1 further comprising substantially contemporaneously measuring an ultrasonic attenuation of the cells and the suspension or slurry.

3. The method of claim 2 wherein an ultrasonic interrogation device is used to measure the ultrasonic attenuation and to detect the backscattered ultrasound.

4. The method of claim 3 wherein the ultrasonic interrogation device includes a transducer positioned to transmit ultrasound towards a reflecting surface, wherein the transducer receives ultrasound which reflects from the reflecting surface, and wherein the transducer receives ultrasound which backscatters from cells that are positioned between the transducer and the reflecting surface.

5. The method of claim 1 wherein a transition in the growth phase of the cells is determined based on backscattering as a function of time.

6. The method of claim 5 wherein the transition is from a logarithmic growth phase to a stationary growth phase.

7. The method of claim 1 wherein the cells are bacteria.

8. The method of claim 1 wherein the cells are yeast cells.

9. The method of claim 1 further comprising interrogating the cells in the suspension or slurry with ultrasound from a focused transducer to produce the backscattered ultrasound.

10. The method of claim 9 wherein the focused transducer defines a focal length and the detected ultrasound backscatters from cells spaced from the transducer a distance between about 50% and 150% of the focal length.

11. The method of claim 1 further comprising calculating an attenuation corrected backscattering amplitude by multiplying a measured backscattering amplitude by a correction factor, wherein the correction factor is a function of a value corresponding to attenuation times distance.

12. A method comprising:
    monitoring fermentation occurring in a fermentor by detecting ultrasound backscattered from cells in a fermentation broth as a function; and
    contemporaneously measuring an ultrasonic attenuation of the cells and the broth, wherein the detecting is with a transducer positioned inside the fermentor.

13. The method of claim 12 further comprising determining a cell growth phase transition based on the detected ultrasound as a function of time.

14. The method of claim 12 wherein detecting the ultrasound backscattered from the cells includes determining amplitude of waveforms in a predetermined time gate.

15. The method of claim 14 wherein the amplitude is a Fourier amplitude.

16. The method of claim 14 wherein the cells are interrogated with ultrasound from a transducer having a focal length and wherein the time gate substantially corresponds to backscattering from cells spaced from the transducer a distance between about 50% and 150% of the focal length.

17. A system comprising:
    a fermenter and a fermentation monitoring system comprising an ultrasonic transducer and a processing device;
    wherein the transducer has a face inside the fermenter such that the contents of the fermenter are free-flowing around the face of the transducer; and wherein the monitoring system is operable to determine ultrasonic backscattering from the contents of the fermenter as a function of fermentation time.

18. The system of claim 17 wherein the monitoring system determines backscattering at a predetermined distance from the transducer face.

19. The system of claim 18 wherein the transducer has a focal length and the predetermined distance is between 50% and 150% of the focal length.

20. The system of claim 17 wherein the processing device is a computer containing programming instructions for determining a transition between growth phases of cells in the fermenter based on changes in the backscattering as a function of time.

21. The system of claim 20 wherein the programming instructions include correcting a measured backscattering response for attenuation effects.

22. The system of claim 21 wherein the correcting involves multiplication by a function of a value representing attenuation times distance.

23. A method comprising determining cell growth during fermentation by monitoring ultrasound backscattered from the cells as a function of time.

24. The method of claim 23 wherein the monitoring is with a transducer positioned inside the fermenter containing the cells and wherein the transducer operates in pulse-echo mode to detect the ultrasound backscattered from the cells.

25. A method comprising monitoring cell size and number per volume during fermentation by monitoring ultrasound backscattered from the cells as a function of time.

26. A method comprising:

monitoring a fermentation process of a population of cells in a suspension or slurry by detecting ultrasound backscattered from the cells in the suspension or slurry; and substantially contemporaneously measuring an ultrasonic attenuation of the cells and the suspension or slurry.

* * * * *

UNITED STATES PATENT AND TRADEMARK OFFICE
CERTIFICATE OF CORRECTION

PATENT NO. : 7,114,375 B2  Page 1 of 1
APPLICATION NO. : 10/757734
DATED : October 3, 2006
INVENTOR(S) : Paul D. Panetta et al.

It is certified that error appears in the above-identified patent and that said Letters Patent is hereby corrected as shown below:

In the Claims:

Column 10, line 43 "as a function;" should read --as a function of time;--

Signed and Sealed this

Thirteenth Day of March, 2007

JON W. DUDAS
*Director of the United States Patent and Trademark Office*